(12) United States Patent
Kidd et al.

(10) Patent No.: US 6,315,446 B1
(45) Date of Patent: Nov. 13, 2001

(54) RADIOLOGY INSTRUMENT

(75) Inventors: Harold James Kidd, Waukesha, WI (US); Bernard Callier, Voisins-le-Bretonneux (FR)

(73) Assignees: GE Medical Systems S.A. (FR); General Electric Company, Schenectady, NY (US)

( * ) Notice: Subject to any disclaimer, the term of this patent is extended or adjusted under 35 U.S.C. 154(b) by 0 days.

(21) Appl. No.: 09/370,314

(22) Filed: Aug. 9, 1999

(30) Foreign Application Priority Data

Sep. 1, 1998 (FR) .................................................. 98 10922

(51) Int. Cl.⁷ ....................................................... H05G 1/02
(52) U.S. Cl. ............................ 378/197; 378/195; 378/196
(58) Field of Search .................................... 378/193, 195, 378/196, 197, 209, 189, 167, 177

(56) References Cited

U.S. PATENT DOCUMENTS

| 4,298,801 | * | 11/1981 | Heitman et al. | 378/197 |
| 4,358,856 | * | 11/1982 | Stivender et al. | 378/197 |
| 4,363,128 | * | 12/1982 | Grady et al. | 379/197 |
| 4,922,512 | * | 5/1990 | Lajus et al. | 379/197 |
| 4,987,585 | * | 1/1991 | Kidd et al. | 379/197 |

FOREIGN PATENT DOCUMENTS 0345138  12/1989  (EP).
0392716  10/1990  (EP).

* cited by examiner

*Primary Examiner*—David P. Porta
(74) *Attorney, Agent, or Firm*—Jay L. Chaskin

(57) ABSTRACT

Radiology instrument comprising an X-ray tube linked with a plane detector. A support device comprises a pedestal of overall L-shape resting on the floor, with a substantially horizontal base, a substantially vertical post and an axis of rotation passing through one end of the base, the post being fixed to the other end of the base and being parallel to the axis, a bracket which is fixed to the top of the post and can rotate about a horizontal axis, and a C-shaped arm which is mounted on the bracket and is capable of rotating about an axis substantially perpendicular to the horizontal axis by sliding on bracket, the tube and the detector being mounted on bow and facing one another, the axis of the bracket the axis of the arm being secant at a point in space referred to as the isocenter. The instrument comprises a means for moving the isocenter continuously along a longitudinal axis of a patient held static.

11 Claims, 3 Drawing Sheets

RADIOLOGY INSTRUMENT

BACKGROUND OF THE INVENTION

The present invention relates to the field of radiology instruments for acquiring images of a patient's body, which are principally usable in the medical field, in particular for cardiac or vascular examinations.

Radiology instruments with three axes of rotation are known, comprising an X-ray tube which is linked with a plane detector arranged opposite the tube and can occupy a plurality of positions in rotation in space around the body. These instruments are generally combined with a table, on which the patient rests and which can be moved in translation in the longitudinal direction of the patient's body, and in the height direction and in rotation about an axis transverse to the patient. The three axes of the radiology instrument are secant at a point which is referred to as the isocenter and on which the images which are obtained are centered.

For cardiac examinations, the region of the patient which is to be viewed is of small size in the length direction. For these examinations, a table with small-amplitude longitudinal travel is therefore used. Conversely, for vascular examinations, it is advantageous to be able to track the propagation of the contrast product which has been injected into the patient's vessels. It is therefore necessary to move the patient from his head to his feet so that each part of the patient passes successively through the isocenter of the radiology instrument. The consequence of this is that a table with large-amplitude longitudinal travel is necessary.

The X-ray tube and the image detector of the radiology instrument are arranged on either side of the patient, one of these elements being in general above the patient and the other below the table, and the table transparent to the X-rays. The space under the table therefore needs to be clear in line with the isocenter in order to not only position one of these elements, but also to move it with different angulations. A table provided with an off-center leg away from the isocenter should therefore be used, with the surface of the table overhanging relative to this leg. Such a table with large-amplitude longitudinal travel is bulky and heavy and undergoes high mechanical stresses. The table surface tends to flex when in the maximum extension position and is supporting a heavy patient, which may compromise the accuracy of the examinations carried out and the patient's comfort. The fact that it overhangs relative to the leg of the table may also be a source of psychological discomfort and stress for the patient. Furthermore, for equivalent technology, a large travel entails a greater motive force, which is a problem for the doctor.

A table is known whose leg is provided with a cam allowing two working positions, which is marketed by the company PHILIPS. The overhang is reduced by this arrangement. Nevertheless, this table may have a tendency to vibrate in response to the external environment, which impairs the accuracy of the examinations. The area which the table passes through when it is being moved from one position to another tends to increase in size and may cause a problem of safety for the staff in charge of handling it, as well as a problem with the cleanliness of the room in which it is located.

A radiology instrument with three axes is also known which is marketed by the company SIEMENS and in which the base is mounted on a cam allowing two longitudinally offset working positions. This instrument has similar drawbacks to the one mentioned above.

BRIEF SUMMARY OF THE INVENTION

It is therefore seen to be desirable to overcome the drawbacks of the known tables.

Thus there is a particular need to provide a radiology instrument which has a high degree of safety and allows full examinations of the patient.

In an embodiment of the invention the radiology instrument comprises an X-ray tube linked with a plane detector the plane of the detector being substantially perpendicular to a line of sight passing approximately through a focus of the tube and through a middle of this plane of the detector. The tube and the detector are capable of occupying positions in rotation around this body by means of a support device. The support device comprises a pedestal of overall L-shape resting on the floor, with a substantially horizontal base, a substantially vertical post and an axis of rotation passing through one end of the base. The post is fixed to the other end of the base and is parallel to the axis. A bracket is fixed to the top of the post and can rotate about a horizontal axis. A C-shaped arm is mounted on the bracket and is capable of rotating about an axis substantially perpendicular to the horizontal axis by sliding on the bracket. The tube and the detector being mounted on the bow and facing one another. The axis of the bracket and the axis of the arm are secant at a point in space referred to as the isocenter.

The instrument comprises means for moving the isocenter continuously along a patient's longitudinal axis. The patient may be held static or moved using the table. It is thus possible to take views with a plurality of relative longitudinal positions of the patient and the isocenter.

Preferably, the base of the pedestal is static in terms of translation relative to the floor. The means for moving the isocenter may be rotary.

Advantageously, an articulation about a substantially vertical fourth axis is arranged in the post, allowing an upper part of the instrument to rotate relative to a lower part of the instrument.

In one embodiment of the invention, isocenter, a point on the axis on the base of the pedestal and a point on the fourth axis form isosceles triangle in a horizontal plane, the base of an the triangle joining the isocenter and the point on the axis of the base of the pedestal.

In one embodiment of the invention the upper part of the instrument comprises the post, the bracket and the C-shaped arm, and the lower part of the instrument comprises the base.

In one embodiment of the invention, the upper part of the instrument comprises the bracket and the C-shaped arm, and the lower part of the instrument comprises the base and the post.

In one embodiment of the invention, the upper part of the instrument comprises a portion of the post, the bracket and the C-shaped arm, and the lower part of the instrument comprises the base and another portion of the post.

In one embodiment of the invention, the means for moving the isocenter is motorized.

The invention also relates to the use of an instrument for taking dynamic images of a static patient.

It is thus possible to use, for angiographic examinations, a table with short longitudinal travel of the type conventionally used for cardiac examinations. The taking of images and the movement of the isocenter can be synchronized so as to track contrast product spreading through the patient's vascular system by moving the X-ray tube and the detector along the patient. It is, of course, possible to combine movement of the table and movement of the isocenter in order to take images from one end of the patient's body to the other. Shifting the isocenter relative to the vertical axis of the base of the radiology instrument makes it possible to increase slightly the possibilities of angulation relative to the patient's body during cardiac examinations.

Finally, when a table is being used which tilts about a horizontal transverse axis arranged in its leg, the isocenter may be brought closer to the leg of the table, which decreases the elevation of the table due to its inclination and reduces the vertical travel needed in order to lower the table enough to maintain a satisfactory position of the patient relative to the isocenter. By reducing the required vertical travel of the table, its mechanical complexity, its mass and its cost are also reduced.

BRIEF DESCRIPTION OF THE DRAWING

The present invention will be understood more clearly from the detailed description of an embodiment taken by way of entirely nonlimiting example and illustrated by the appended drawings, in which.

DETAILED DESCRIPTION OF THE INVENTION

Figure 1:
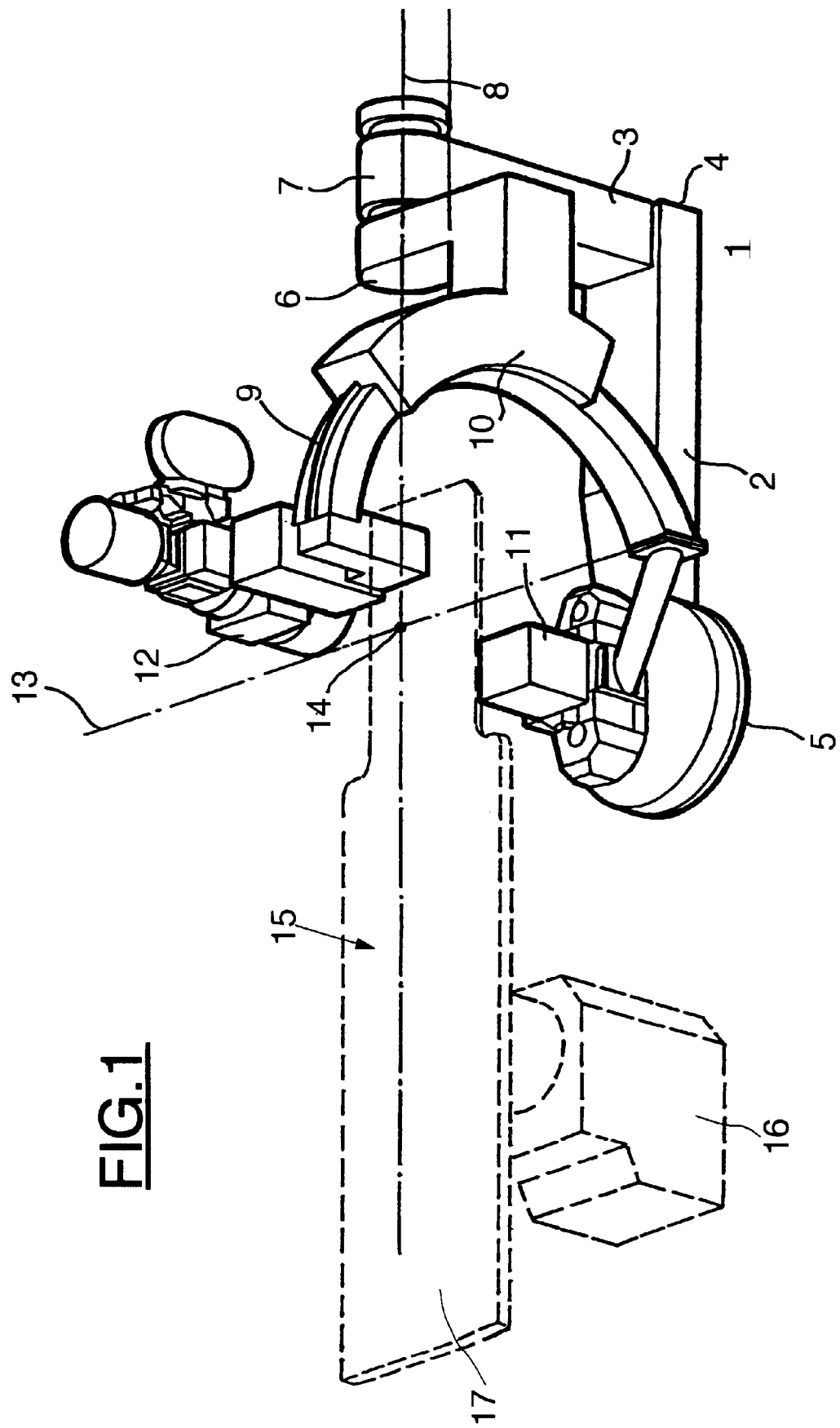
FIG. 1 is a perspective view of a radiology instrument according to the prior art.

FIG. 1 shows a radiology instrument comprising an L-shaped pedestal 1. This pedestal 1 is provided with a substantially horizontal base 2 and a substantially vertical post 3. The post is fixed to one end 4 of the base 2. At another end 5, the base 2 is provided with a vertical axis of rotation parallel to the post 3. In one example, the pedestal can rotate relative to a reference orientation by plus or minus 95°.

The instrument also comprises a bracket 6. The bracket 6 is fixed by a first end in terms of rotation on the top 7 of the post 3. The axis of rotation 8 of the bracket 6 is horizontal. Its amplitude of rotation, in one example, is plus or minus 105° around a medium position. The bracket 6 has a bayonet-shaped appearance.

A C-shaped arm 9 is supported so as to slide in rotation by another end 10 of bracket 6. The arm 9 holds, diametrically opposite one another, an X-ray tube 11 and a image detector 12. The detector 12 has a plane detection surface. A line of sight is determined by a straight line joining a focus of the tube 11 to a mid-point of the plane of detector 12. The arm 9 can rotate by sliding in the end 10 about an axis 13. In one example, around a medium neutral position, arm 9 can rotate by plus 45° to minus 50°.

The three axes of rotation of pedestal 1, of bracket 6 and of arm 9 are isocentered. They meet at a point 14 in space. In the medium position, these three axes are perpendicular to one another. In view of the bayonet nature of bracket 6 represented, tube 11 and detector 12 are mounted laterally on diametric ends of arm 9.

A patient is intended to lie on a patient-support table 15, the longitudinal orientation of which is intended to be aligned with the axis 8 when the orientation of pedestal 1 is neutral: 0° . The table 15 comprises a leg 16 on top of which there is a surface 17 on which the patient rests. The surface 17 can be moved longitudinally along an axis which coincides with axis 8 in the neutral position illustrated in FIG. 1. The surface 17 can also be moved heightwise and may possibly be tilted about a transverse axis which is parallel to the axis 13 in the neutral position, illustrated in FIG. 1, by means of an articulation (not shown) arranged between surface 17 and leg 16.

Figure 2:
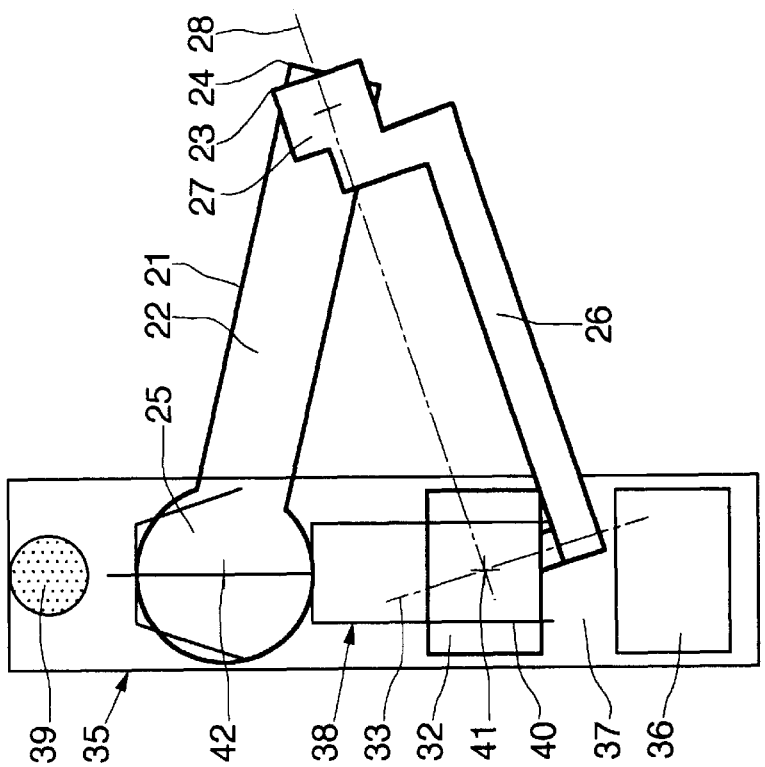
FIG. 2 is a schematic plan view of a radiology instrument and a table according to the prior art.
Figure 3:
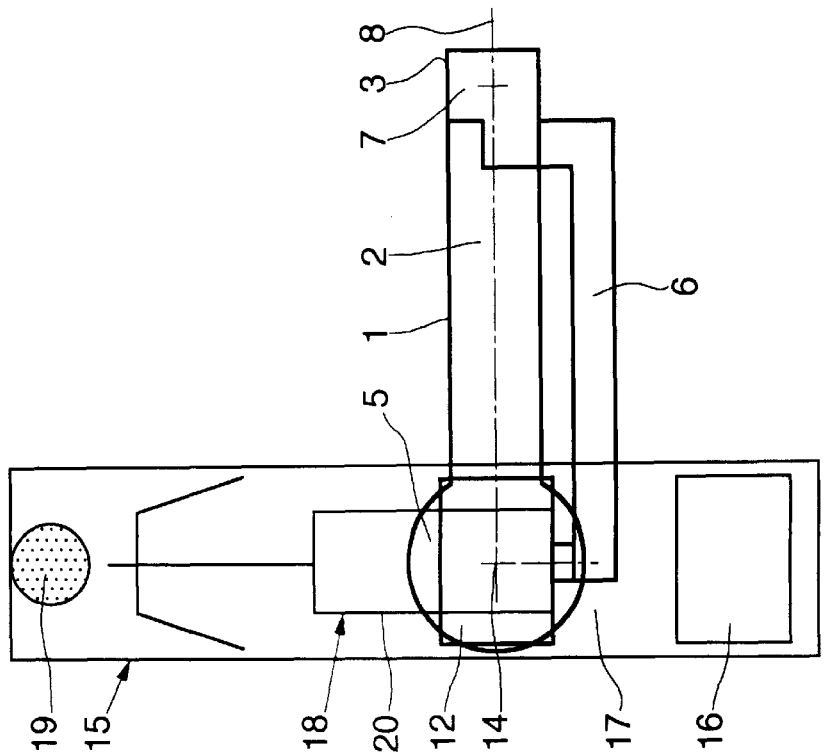
FIG. 3 is a schematic plan view of a radiology instrument and a table according to an embodiment of the invention.

FIG. 2 shows the relative positions of radiology instrument and the table 15 when carrying out a vascular examination of a patient, referenced 18 and represented schematically, with a head 19 and feet 20. The surface 17 is represented in a position which is used to take images of feet 20 of the patient 18. The surface 17 is in the maximum extension position with a considerable overhang relative to the legs 15. It can be seen that such an overhang, in particular with heavy patients, weighing up to 250 kg, causes problems with mechanical stresses in the table 15, in the leg 16 and for fixing the leg 16 in the floor of the room in which it is installed.

With such a radiology instrument according to the prior art, the isocenter 14 is fixed relative to the leg 16.

In the following figures, which illustrate the invention, the references of those elements which are similar to the ones in the previous figures have had 10 the number 20 added to them.

The radiology instrument comprises a fourth articulation, arranged on post 23 and allowing bracket 26 to rotate relative to pedestal 21. The articulation may be provided between base 22 and post 23 of pedestal 21, or between a lower part and an upper part of the post 23, or alternatively 25 between post 23 and bracket 26. The axis of this articulation is vertical and parallel to vertical axis 42 about which pedestal 21 rotates.

When pedestal 21 is rotated by a given angle a about its axis 42 and bracket 26 by an opposite angle of the same value -a about its vertical axis, the isocenter 41, consisting of the intersection of axis 28 and axis 33 of C-shaped arm (not shown in FIG. 2) can be made to follow a straight line parallel to the longitudinal axis of the patient 38. The result of this arrangement is that it is possible to run along a certain length of the body of patient 38 by virtue of the angle which axis 28 of bracket 26 forms relative to the axis of base 22 of pedestal 21 which joins vertical axis 42 with the vertical.axis of the articulation of post 23.

It is thus possible to use a shorter table 35, for example of the type used for cardiac examinations, which gives a reduction in the size of the overall device, a decrease in the mechanical stresses in the table, which leads to a weight saving and a decrease in cost while ensuring better comfort for the patient, and a better quality of examination because of the reduction in the overhang and therefore the flexing of the table.

Figure 4:
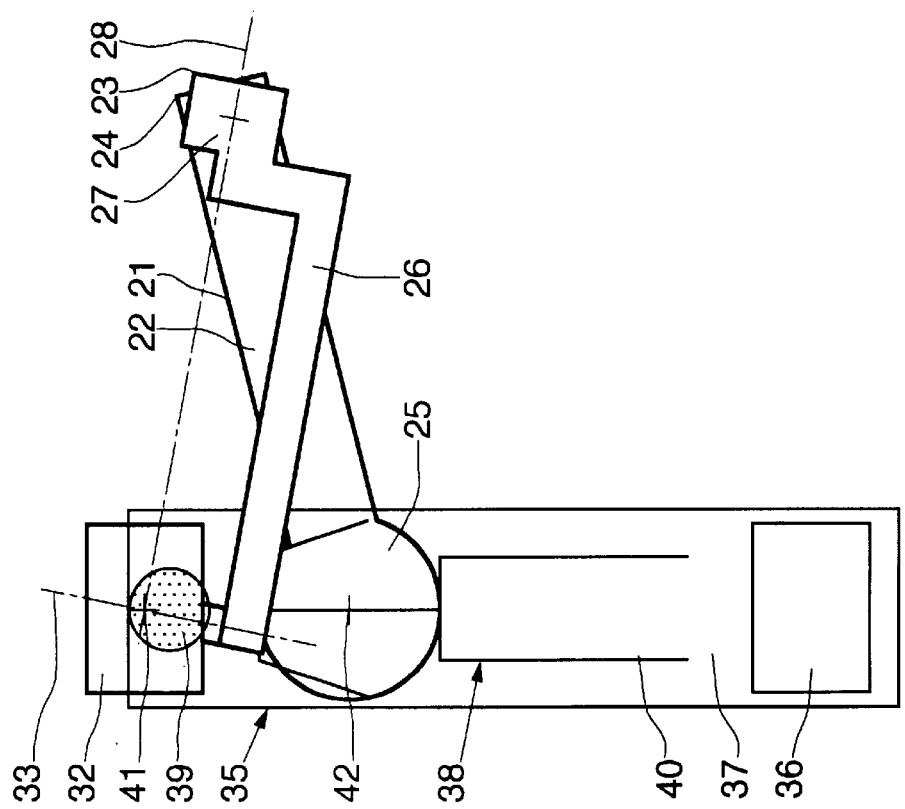

FIG. 4 illustrates the movement of isocenter 41 in the opposite patient's head 39. For example, provided to move isocenter the order of 0.8 m, which will be subtracted from the overhanging longitudinal motion required of table 35.

Figure 5:
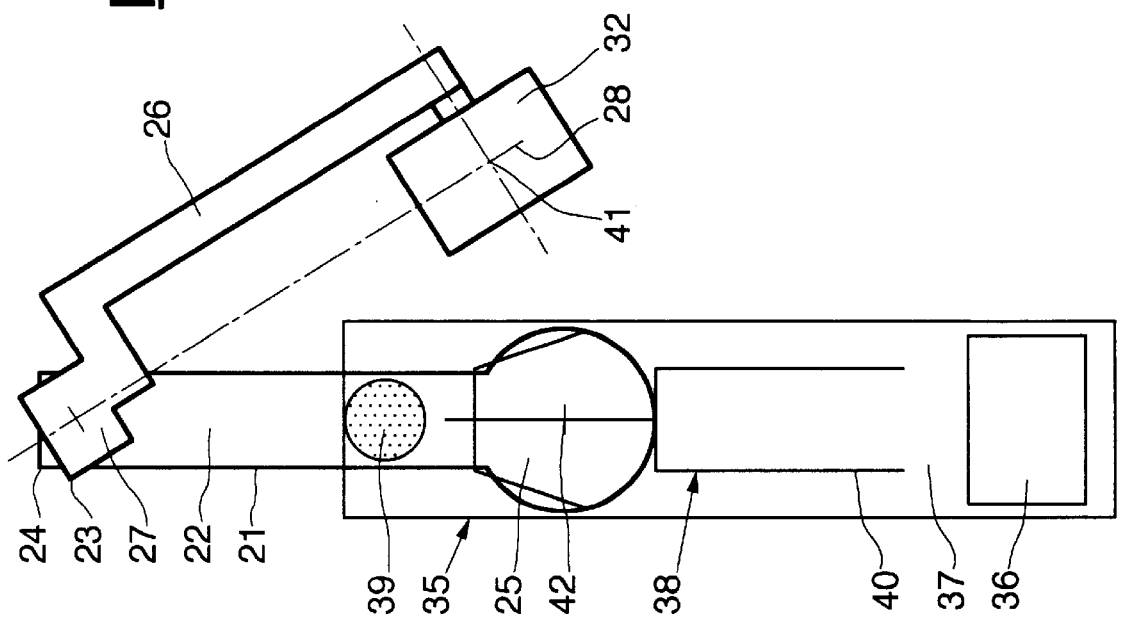
FIGS. 4 and 5 are similar views to FIG. 3 showing the possibilities for using the invention.

FIG. 5 illustrates an embodiment where it is possible to fully clear the table 35. In order to do this, pedestal 21 is returned into a neutral position such that axis 28 is aligned with longitudinal axis of surface 27, and bracket 26 is then made to rotate about the vertical axis of the articulation arranged in post 23. This arrangement makes it possible to clear the X-ray tube and the detector away to the side of table 35 and facilitate access to patient 38, which may prove very useful for emergency interventions, such as resuscitation, carried out on the patient 38.

By virtue of the invention, a table with a construction much simpler than that used to date can be used for angiographic examinations. The safety of the instrument is satisfactory since the leg of the table and the axis of rotation of the base of the radiology instrument are fixed. Cleaning of these instruments in the room in which they are located is also facilitated.

Various modifications in structure and/or steps and/or function may be made by one skilled in the art to the disclosed embodiments without departing from the scope and extent of the invention.

What is claimed is:

1. A radiology instrument comprising an X-ray tube linked with a detector, a plane of the detector being substantially perpendicular to a line of sight passing approximately through a focus of the tube and through a middle of plane of the detector, the tube and the detector being capable of occupying positions in rotation around a body by means of a support device, the support device comprising a pedestal of overall L-shape resting on a floor, with a substantially horizontal base, a substantially vertical post and an axis of rotation passing through one end of the base, the post being fixed to the other end of the base and being parallel to said axis of rotation, an articulation about a substantially vertical fourth axis arranged in said post allowing an upper part of the instrument to rotate about said fourth axis relative to a lower part of the instrument, a bracket which is fixed to the top of the articulated post and can rotate about a horizontal axis, and a C-shaped arm mounted on the bracket and capable of rotating about an axis substantially perpendicular to said horizontal axis by sliding on the bracket, the tube and the detector being mounted on said C-shaped arm and facing one another, the axis of the bracket and the axis of the arm being secant at a point in space referred to as the isocenter and means for moving the isocenter continuously along a longitudinal axis of the body.

2. Instrument according to claim 1, wherein the base of the pedestal is static in terms of translation relative to the floor.

3. Instrument according to claim 1, wherein the means for moving the isocenter is rotary.

4. Instrument according to claim 2, wherein the means for moving the isocenter is rotary.

5. Instrument according to claim 1, wherein the isocenter, a point on the axis on the base of the pedestal and a point on the fourth axis form an isosceles triangle in a horizontal plane, the base of the triangle joining the isocenter and the point on the axis of the base of the pedestal.

6. Instrument according to claim 1, wherein the upper part of the instrument comprises the bracket and the C-shaped arm, and in that the lower part of the instrument comprises the base and the post.

7. Instrument according to claim 2, wherein the upper part of the instrument comprises the bracket and the C-shaped arm, and in that the lower part of the instrument comprises the base and the post.

8. Instrument according to claim 1, wherein the upper part of the instrument comprises a portion of the post, the bracket and the C-shaped arm, and in that the lower part of the instrument comprises the base and another portion of the post.

9. Instrument according to claim 1, wherein the means for moving the isocenter is motorized.

10. Use of an instrument according to claim 1 for taking dynamic images of a static body.

11. A radiology instrument comprising an X-ray tube linked with a detector, a plane of the detector being substantially perpendicular to a line of sight passing approximately through a focus of the tube and through a middle of plane of the detector, the tube and the detector being capable of occupying positions in rotation around a body by means of a support device, the support device comprising a pedestal of overall L-shape resting on a floor, with a substantially horizontal base, a substantially vertical post and an axis of rotation passing through one end of the base, the post being fixed to the other end of the base and being parallel to said axis of rotation, an articulation about a substantially vertical fourth axis arranged in said post allowing an upper part of the instrument to rotate about said fourth axis relative to a lower part of the instrument, a bracket which is fixed to the top of the articulated post and can rotate about a horizontal axis, and a C-shaped arm mounted on the bracket and capable of rotating about an axis substantially perpendicular to said horizontal axis by sliding on the bracket, the tube and the detector being mounted on said C-shaped arm and facing one another, the axis of the bracket and the axis of the arm being secant at a point in space referred to as the isocenter and means for moving the isocenter continuously along a longitudinal axis of the body and wherein the upper part of the instrument comprises the post, the bracket and he C-shaped arm, and the lower part of the instrument comprises the base.

* * * * *